(12) United States Patent
Fallone et al.

(10) Patent No.: US 8,958,528 B2
(45) Date of Patent: *Feb. 17, 2015

(54) REAL-TIME DOSE RECONSTRUCTION USING DYNAMIC SIMULATION AND IMAGE GUIDED ADAPTIVE RADIOTHERAPY

(75) Inventors: B. Gino Fallone, Edmonton (CA); Marco Carlone, Edmonton (CA); Brad Murray, Sherwood Park (CA)

(73) Assignee: Alberta Health Services, Edmonton, Alberta (CA)

( * ) Notice: Subject to any disclaimer, the term of this patent is extended or adjusted under 35 U.S.C. 154(b) by 300 days.

This patent is subject to a terminal disclaimer.

(21) Appl. No.: 13/305,123

(22) Filed: Nov. 28, 2011

(65) Prior Publication Data

US 2012/0069962 A1 Mar. 22, 2012

Related U.S. Application Data

(63) Continuation of application No. 12/090,591, filed as application No. PCT/CA2006/001655 on Oct. 10, 2006, now Pat. No. 8,073,102.

(60) Provisional application No. 60/726,612, filed on Oct. 17, 2005.

(51) Int. Cl.
*A61N 5/10* (2006.01)

(52) U.S. Cl.
CPC .............. *A61N 5/103* (2013.01); *A61N 5/1048* (2013.01); *A61N 5/1037* (2013.01); *A61N 5/1049* (2013.01); *A61N 5/1067* (2013.01); *A61N 2005/1055* (2013.01); *A61N 2005/1072* (2013.01)

USPC .......................................................... 378/65

(58) Field of Classification Search
USPC .......................................................... 378/65
See application file for complete search history.

(56) References Cited

U.S. PATENT DOCUMENTS

| 5,422,926 | A | 6/1995 | Smith et al. |
| 5,434,420 | A | 7/1995 | McKeown et al. |
| 5,538,494 | A | 7/1996 | Matsuda |
| 5,651,043 | A | 7/1997 | Tsuyuki et al. |
| 5,851,182 | A | 12/1998 | Sahadevan |
| 5,977,530 | A | 11/1999 | Bessho et al. |
| 6,175,761 | B1 | 1/2001 | Frandsen et al. |

(Continued)

FOREIGN PATENT DOCUMENTS

| CA | 2616272 A1 | 2/2007 |
| WO | WO 01/74440 | 10/2001 |

(Continued)

OTHER PUBLICATIONS

International Search Report and Written Opinion of the International Searching Authority for International Application No. PCT/CA2006/001656.

(Continued)

*Primary Examiner* — Allen C. Ho
(74) *Attorney, Agent, or Firm* — Alston & Bird LLP

(57) ABSTRACT

A radiation therapy treatment method comprises imaging a subject and simulating four-dimensional aspects of radiotherapy. A treatment plan based on the simulation is generated to permit real-time, three-dimensional dose reconstruction at the time of treatment. The simulation and treatment plan are used during treatment fractions to achieve real-time image guidance.

24 Claims, 4 Drawing Sheets

(56) References Cited

U.S. PATENT DOCUMENTS

| | | | |
|---|---|---|---|
| 6,198,957 | B1 | 3/2001 | Green |
| 6,366,641 | B1 | 4/2002 | Whitham |
| 6,366,798 | B2 | 4/2002 | Green |
| 6,708,054 | B2 | 3/2004 | Shukla et al. |
| 6,862,469 | B2 | 3/2005 | Bucholz et al. |
| 6,993,112 | B2 * | 1/2006 | Hesse ............... 378/65 |
| 7,221,733 | B1 * | 5/2007 | Takai et al. ............ 378/65 |
| 7,227,925 | B1 * | 6/2007 | Mansfield et al. .......... 378/65 |
| 7,245,698 | B2 * | 7/2007 | Pang et al. ............ 378/65 |
| 7,289,599 | B2 * | 10/2007 | Seppi et al. ............ 378/65 |
| 7,349,522 | B2 * | 3/2008 | Yan et al. ............ 378/65 |
| 7,352,370 | B2 | 4/2008 | Wang et al. |
| 7,375,357 | B2 | 5/2008 | Kaufman |
| 7,415,095 | B2 * | 8/2008 | Wofford et al. ............ 378/65 |
| 7,443,946 | B2 | 10/2008 | Deller et al. |
| 7,450,687 | B2 * | 11/2008 | Yeo et al. ............ 378/65 |
| 7,453,976 | B1 * | 11/2008 | Yin ............... 378/9 |
| 7,551,717 | B2 | 6/2009 | Tome et al. |
| 7,567,694 | B2 | 7/2009 | Lu et al. |
| 7,574,251 | B2 * | 8/2009 | Lu et al. ............ 600/427 |
| 7,596,207 | B2 * | 9/2009 | Kaus et al. ............ 378/65 |
| 7,609,810 | B2 | 10/2009 | Yi et al. |
| 7,639,854 | B2 | 12/2009 | Schnarr et al. |
| 7,643,661 | B2 | 1/2010 | Ruchala et al. |
| 7,853,308 | B2 * | 12/2010 | Sauer et al. ............ 600/425 |
| 7,989,987 | B2 | 8/2011 | McDonald |
| 8,042,209 | B2 * | 10/2011 | D'Souza et al. ............ 5/610 |
| 8,073,102 | B2 * | 12/2011 | Fallone et al. ............ 378/65 |
| 8,229,068 | B2 * | 7/2012 | Lu et al. ............ 378/65 |
| 2001/0001807 | A1 | 5/2001 | Green |
| 2001/0049474 | A1 | 12/2001 | Wagshul |
| 2002/0123682 | A1 | 9/2002 | Allred et al. |
| 2003/0004405 | A1 | 1/2003 | Townsend et al. |
| 2003/0174808 | A1 | 9/2003 | Hughes et al. |
| 2005/0197564 | A1 | 9/2005 | Dempsey |
| 2005/0201516 | A1 | 9/2005 | Ruchala et al. |

FOREIGN PATENT DOCUMENTS

| | | | | |
|---|---|---|---|---|
| WO | WO 03/076016 A1 * | 9/2003 | ............ | A61N 5/10 |
| WO | WO 2004/024235 A1 | 3/2004 | | |
| WO | WO 2005/031629 | 4/2005 | | |
| WO | WO 2007/014026 A2 * | 2/2007 | ............ | A61N 5/10 |
| WO | WO 2007/014105 A2 * | 2/2007 | ............ | A61N 5/10 |

OTHER PUBLICATIONS

Office Action for U.S. Appl. No. 12/090,586 dated Jun. 10, 2011.
Office Action for European Application No. 06 790 814.5 dated Nov. 13, 2009.
Office Action for Chinese Application No. 20060046233.9 dated Mar. 10, 2010.
Kirkby, C. et al., *Patent Dosimetry for Mybrid MRI-Radiotherapy Systems*, Med. Phys. vol. 35, No. 3, Mar. 2008, pp. 1019-1027.
Bielajew, A. F., *The Effect of Strong Longitudinal Magnetic Fields on Dose Deposition From Electron and Photon Beams*, Med. Phys. vol. 20, No. 4, Jul./Aug. 1993, pp. 1171-1179.
Supplementary European Search Report for EP 06 79 0814 completed Aug. 27, 2009.
International Search Report and Written Opinion of the International Searching Authority for International Application No. PCT/CA2006/001655.
Office Action for U.S. Appl. No. 12/090,586 dated Feb. 13, 2012.
United States Office Action for U.S. Appl. No. 12/090,586, dated Aug. 26, 2013.
Raaymakers, B., *Integrating a MRI Scanner with a 6 MV Radiotherapy Accelerator: Dose Deposition in a Transverse Magnetic Field*, Med. Biol. 49 (2004) pp. 4109-4118.
Office Action from U.S. Appl. No. 12/090,586 mailed Nov. 14, 2014.
Marbach, J.R.; "Management of Radiation Oncology Patients with Implanted Cardiac Pacemakers"; *AAPM Report No. 45* (1994); Medical Physics vol. 21, Issue 1 (1994).
Office Action from Canadian Patent Application No. 2,626,536 dated Sep. 17, 2014.
Office Action from Japanese Patent Application No. 2013-097688 dated Oct. 7, 2014.

* cited by examiner

REAL-TIME DOSE RECONSTRUCTION USING DYNAMIC SIMULATION AND IMAGE GUIDED ADAPTIVE RADIOTHERAPY

CROSS-REFERENCE TO RELATED APPLICATIONS

This application is a continuation of U.S. application Ser. No. 12/090,591, filed Oct. 23, 2008, now U.S. Pat. No. 8,073,102, which was a national phase entry of International Application No. PCT/CA2006/001655, filed Oct. 10, 2006, which claims priority to U.S. Provisional Application No. 60/726,612, filed Oct. 17, 2005, all of which are hereby incorporated herein in its entirety by reference.

FIELD OF THE INVENTION

The present invention relates generally to radiation therapy and in particular to real-time dose reconstruction using dynamic simulation and image guided adaptive radiotherapy.

BACKGROUND OF THE INVENTION

Radiation therapy can be given to treat proliferative tissue disorders including but not limited to cancer, arteriovenous malformations, dermatological legions etc. During radiation therapy, the tissue of the patient known to or suspected to contain the disease is exposed to radiation. Linear accelerators are commonly used to irradiate a target volume encompassing the tissue to be treated during radiation therapy. As is known, linear accelerators use microwave technology to accelerate electrons in a waveguide and then allow the electrons to collide with a heavy metal target. As a result of the collisions, high-energy x-rays are scattered from the target. A portion of the scattered x-rays is collected and shaped by a beam collimating device to form an output beam of radiation conforming to the shape of the target volume. The linear accelerator also includes a gantry that rotates around the patient allowing the output beam of radiation to be delivered to the desired target volume from any angle by rotating the gantry.

Prior to exposing a patient to radiation, a treatment plan is typically developed in order to determine accurately the location of the tissue to be treated and how best to treat the tissue with radiation. Many imaging techniques have been used in treatment planning such as for example, computed tomography (CT), magnetic resonance imaging (MRI), and nuclear scintigraphy including single photon emission tomography (SPECT) and positron emission tomography (PET). Acquired images of the tissue are used to define the target volume so that the actual tissue irradiated by the output beam of radiation conforms as much as possible to the target volume. In many instances, the images of the tissue used to define the target volume are acquired in a single simulation.

For dose delivery, techniques such as tumour immobilisation with IMRT and image guidance have commonly been utilized. The purpose of image guidance is to ensure that the target tissue is placed at the isocenter of the linear accelerator at the beginning of radiation treatment. In tissue sites where a large amount of tissue motion is expected (for instance lung cancer radiotherapy), image guided therapy also constitutes control of the output beam of radiation to ensure that the irradiation time is restricted to the moment when the tissue is localized at the linear accelerator isocenter.

Unfortunately, this method has a fundamental difficulty if the image used to define the target volume is acquired in a single simulation since it is not known if image guided reproduction of the target location in subsequent treatment fractions results in the planned dosimetry being accurately delivered to the target and non-target tissues. This is because it is not known, a priori, if the single simulation image is representative of the patient positioning and target volume configuration in subsequent radiotherapy treatment fractions.

To provide more accurate position information concerning the target tissue and ensure the beam of radiation is properly directed in subsequent radiotherapy treatment fractions, it has been considered to integrate a linear accelerator with a magnetic resonance imaging apparatus.

MRI is a well-known imaging technique. During MRI, a target, typically a human patient, is placed into an MRI machine and subjected to a uniform magnetic field produced by a polarizing magnet housed within the MRI machine. Radio frequency (RF) pulses, generated by an RF coil housed within the MRI machine in accordance with a particular localization method, are used to scan target tissue of the patient. MRI signals are radiated by excited nuclei in the target tissue in the intervals between consecutive RF pulses and are sensed by the RF coil. During MRI signal sensing, gradient magnetic fields are switched rapidly to alter the uniform magnetic field at localized areas thereby allowing spatial localization of MRI signals radiated by selected slices of the target tissue. The sensed MRI signals are in turn digitized and processed to reconstruct images of the target tissue slices using one of many known techniques.

Unfortunately, even in such systems which use inter-fraction image guidance, tissue motion during the treatment fraction results in the delivered dose of radiation differing from the planned dose, and necessitates the use of a planning target volume (PTV) to ensure tissue coverage. The consequence is that the normal tissue surrounding the target tissue also receives an additional radiation dose.

Further, real-time, three-dimensional (3D) imaging of the patient during the radiation therepy has not been incorporated into IMRT delivery devices, and so it does not allow for true radiation dose reconstruction post treatment. The current art only calculates a post-treatment radiation dose reconstruction based on a pre-treatment static image of the target volume.

In addition, while it is desirable to have real-time imaging during radiotherapy, the true quantity of interest is the real-time accumulation of radiation doses to all structures in the target volume. Real-time dose-accumulation data could be used to detect treatment errors at a very early time, and would allow intervention in the instance where the treatment fraction dose is outside of tolerance. This is not currently available since no method of radiation dose calculation is currently fast enough (unless prohibitively large numbers of parallel processing computers are used) to perform the necessary dose accumulation calculations in real-time. As well, the availability of real-time radiation dose calculation would allow safe dose escalation in those tissue sites where the optimal dose has not yet been defined.

As will be appreciated, improved radiation therapy techniques which obviate or mitigate one or more of the above-referenced problems are desired. It is therefore an object of the present invention to provide a novel real-time dose reconstruction using dynamic simulation and image guided adaptive radiothereapy.

SUMMARY OF THE INVENTION

According to one aspect there is provided a radiation therapy treatment method comprising:

imaging a subject and simulating four-dimensional aspects of radiotherapy;

generating a treatment plan based on the simulation thereby to permit real-time, three-dimensional dose reconstruction at the time of treatment; and using the simulation and treatment plan during treatment fractions to achieve real-time image guidance.

In one embodiment, a high resolution, three-dimensional MRI apparatus is used to simulate the radiotherapy treatment by processing, in three-dimensions and in real-time, the target volume and the maximum possible extensions of the target volume that are likely to occur during the treatment. In certain clinical target tissue sites, this process is repeated several times on several days.

A four-dimensional treatment plan is calculated based on the mean trajectory of the target volume determined from the four-dimensional simulation. The range of likely deviations of the target volume from the mean trajectory of the target volume is also determined and a bank of three-dimensional dose distributions that cover the range of likely deviations of the target volume is calculated.

The target volume is tracked in three-dimensions and in real-time during radiotherapy treatment. Images generated using an MRI apparatus, which is interfaced to a linac, are used to track the target volume. Real-time dose distributions (i.e. four-dimensional dose distributions) are calculated at the time of treatment by drawing from information that is available from the treatment plan.

According to another aspect there is provided a computer-readable medium embodying a computer program for radiation therapy treatment, said computer program comprising:

computer program code for simulating four-dimensional aspects of radiotherapy based on subject images;

computer program code for generating a treatment plan based on the simulation thereby to permit three-dimensional dose reconstruction; and computer program code for guiding irradiation during treatment fractions.

BRIEF DESCRIPTION OF THE DRAWINGS

Embodiments will now be described more fully with reference to the accompanying drawings in which.

DETAILED DESCRIPTION OF PREFERRED EMBODIMENTS

A radiation therapy treatment method initially requires imaging of a subject and simulating four-dimensional aspects of radiotherapy. A treatment plan is generated based on the simulation such that real-time, three-dimensional radiation dose reconstruction is possible at the time of treatment. The simulation and treatment plan are used during treatment fractions to achieve real-time image guidance. Further specifics concerning the radiation therapy treatment method will now be described with reference to FIGS. 1 to 5.

Figure 1:
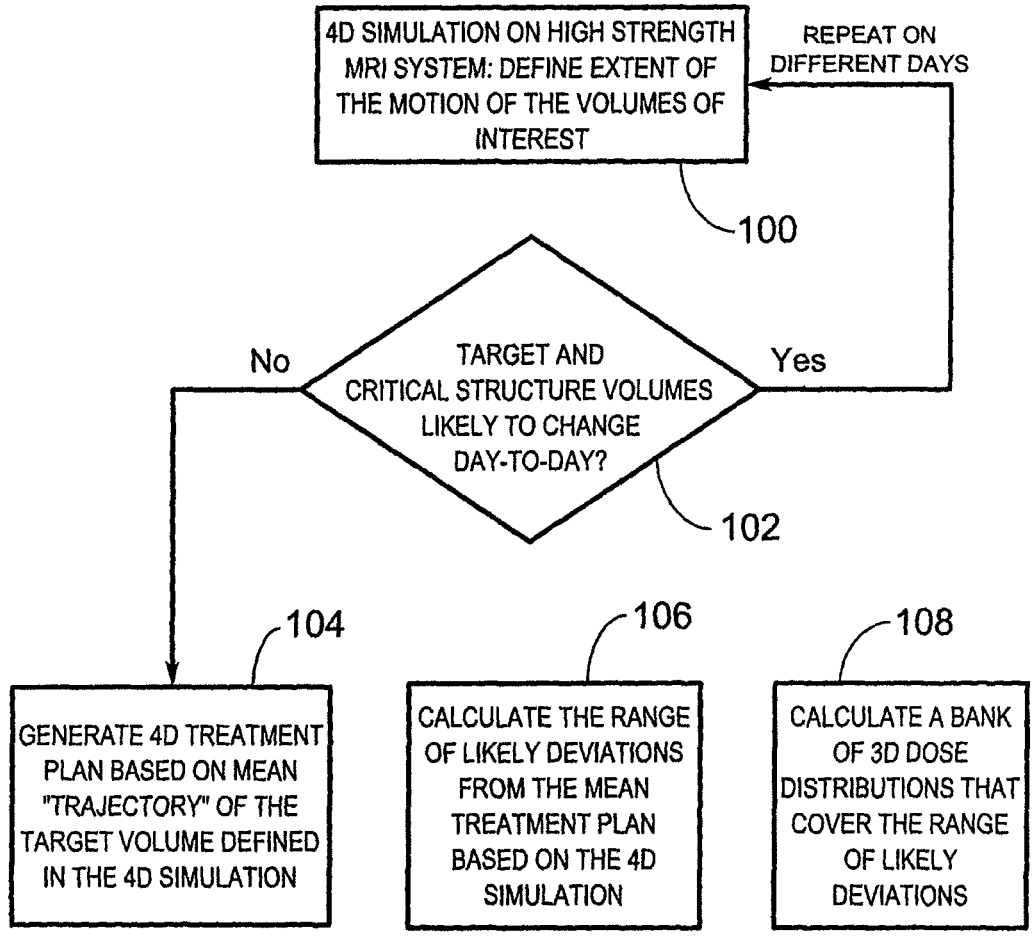
FIG. 1 is a flowchart showing the steps performed during radiotherapy simulation and treatment plan generation.

As mentioned above, initially a four-dimensional (4D) radiotherapy simulation procedure is performed whereby the goal of the radiotherapy simulation is to determine the likely configuration and real-time three-dimensional motion (at the time of treatment) of a target volume, and other volumes that are critical for the success of the radiation therapy ("critical volumes"). This is accomplished by using an imaging modality that is capable of providing soft-tissue contrast and a three-dimensional, real-time imaging that can be registered to a subsequent treatment imaging device. In this particular embodiment, a high strength (for example 1.5 to 3 T) MRI apparatus is used to capture images of the target and critical volumes. Those of skill in the art will however appreciate that any suitable imaging modality may be used. The steps performed during the radiotherapy simulation procedure are shown in FIG. 1.

During the radiotherapy simulation procedure, acquired images are processed using computer software. In particular, during processing, the maximum possible target and critical volume movements that are likely to occur during radiotherapy treatment are determined (step 100). The imaged target and critical volumes are then examined to determine if the target and critical volumes are likely to change day-to-day (step 102). If not, a 4D treatment plan is generated based on the mean trajectory of the target and critical volumes (step 104) as will be described. At step 102, if the target and critical volumes are likely to change day-to-day, step 100 is repeated several times over a number of days.

The purpose of the radiotherapy simulation procedure is not to configure the patient such that a reproducible target volume position can be determined. Rather, the purpose of the radiotherapy simulation procedure is to define a patient configuration that can be reliably reproduced during subsequent radiotherapy treatment, and further to measure the target and critical volume motion that is likely to be present during the subsequent radiotherapy treatment. The result of the radiotherapy simulation procedure is the definition of a patient position (legs, torso, arms, head, any form of immobilisation, etc) that is reproduced at the time of treatment, as well as a measurement of the mean three-dimensional trajectory of internal tissue structures of the patient. Expected deviations from the average target and critical volume positions are also quantified such that the actual target and critical volume positions at the time of treatment can be estimated with a high degree of confidence.

By performing the radiotherapy simulation procedure, more accurate position data concerning the target and critical volumes within the patient is known at the time of treatment. This has the benefit that the selected treatment plan is based on a patient configuration that is more likely to be realized at the time of treatment unlike conventional radiotherapy that is based on the assumption that a static target volume position is reproduced at each treatment fraction.

As mentioned above, with the mean three-dimensional trajectory of internal tissue structures determined through the radiotherapy simulation procedure, the 4D treatment plan is created that specifically makes use of the mean three-dimensional trajectory of the target and critical volumes (step 104). The treatment plan is inherently four-dimensional, in that it explicitly accounts for target and critical volume motion (over a respiratory cycle, for example) at the time of treatment planning. The treatment plan therefore produces photon fluence distributions, and image guidance parameters to be used during radiation exposure at the time of treatment. This treatment planning is based on currently available three-dimensional treatment planning dosimetry. The range of expected deviations to the average target and critical volume positions that were measured during the four-dimensional radiotherapy simulation imaging are also calculated (step 106).

With the 4D treatment plan generated and the range of expected deviations to the average target and critical volume positions calculated, a bank of patient specific, three-dimensional radiation dose distributions that cover the range of expected deviations of the average target and critical volume positions are calculated and stored as data files (step 108). Thus, the data files include the treatment plan, as well as sufficient information that allows real-time dose reconstruction by correlation of observed variances to the treatment plan to pre-calculated perturbations of the treatment plan. The data files are then subsequently used by an integrated linear accelerator ("linac") and MRI system during radiation dose delivery in order to compute 3D dose with sufficient speed so as to allow real-time radiation dose calculation with modest computing power as will be described.

Figure 2:
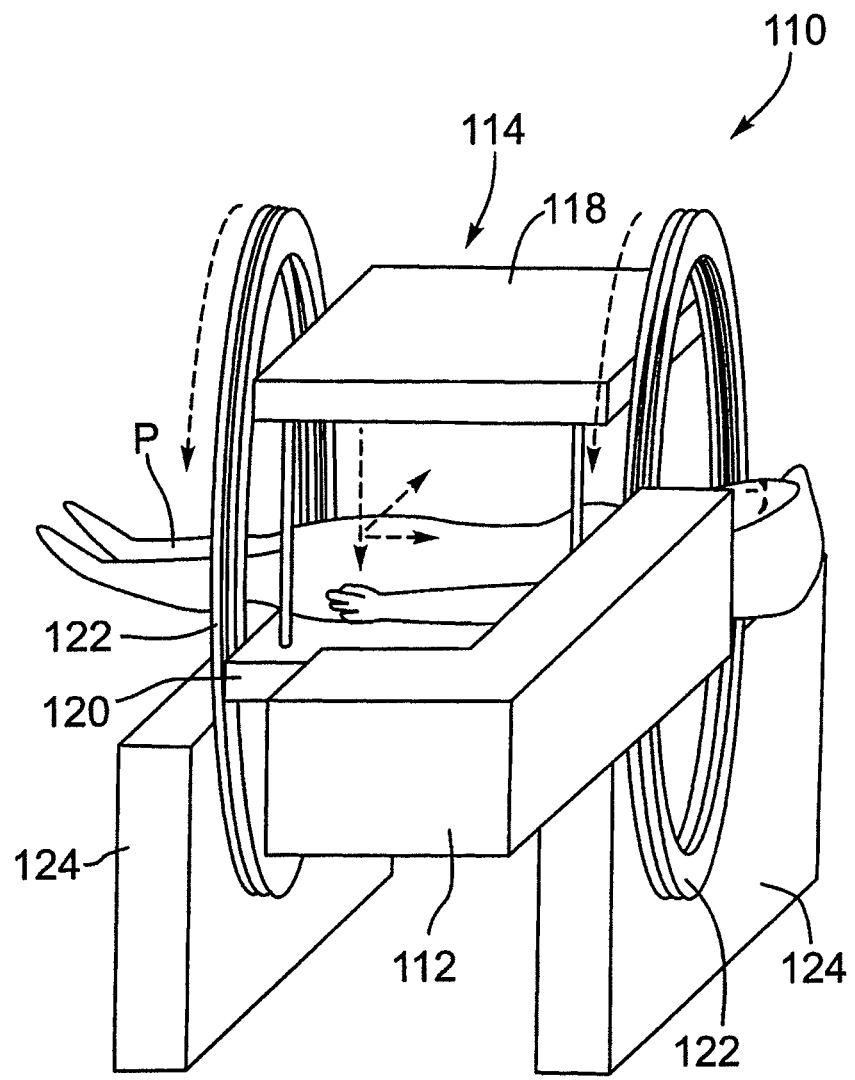
FIG. 2 is a partial schematic, perspective view of an integrated linear accelerator and MRI system in one orientation.
Figure 3:
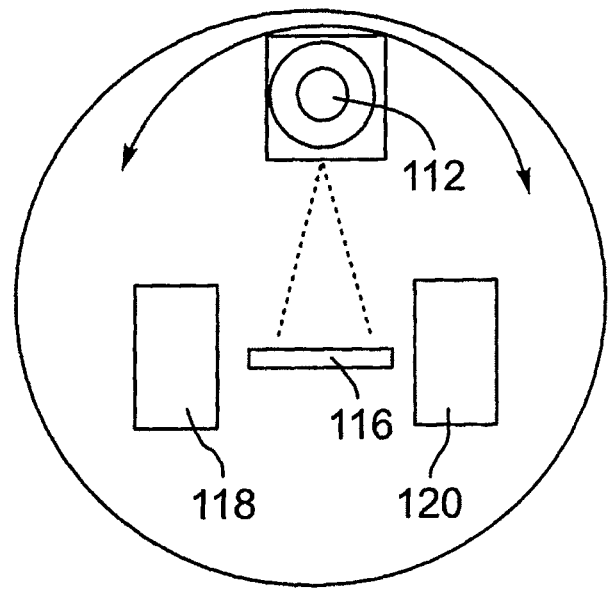
FIG. 3 is a view in a transverse plane of the integrated linear accelerator and MRI system of FIG. 2 in another orientation.
Figure 4:
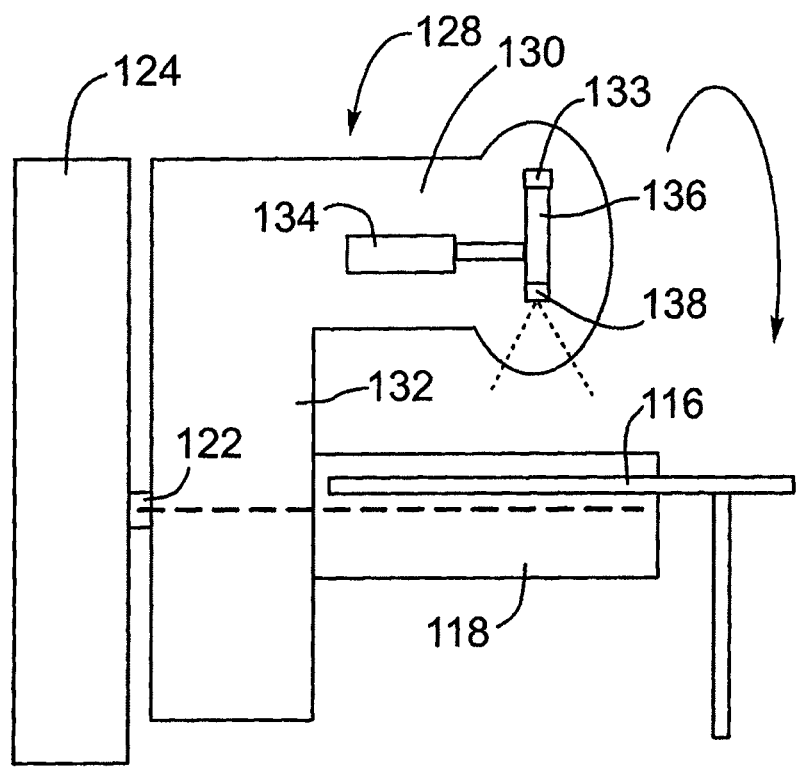
FIG. 4 is a view in a saggital plane of the integrated linear accelerator and MRI system of FIG. 3.
Figure 5:
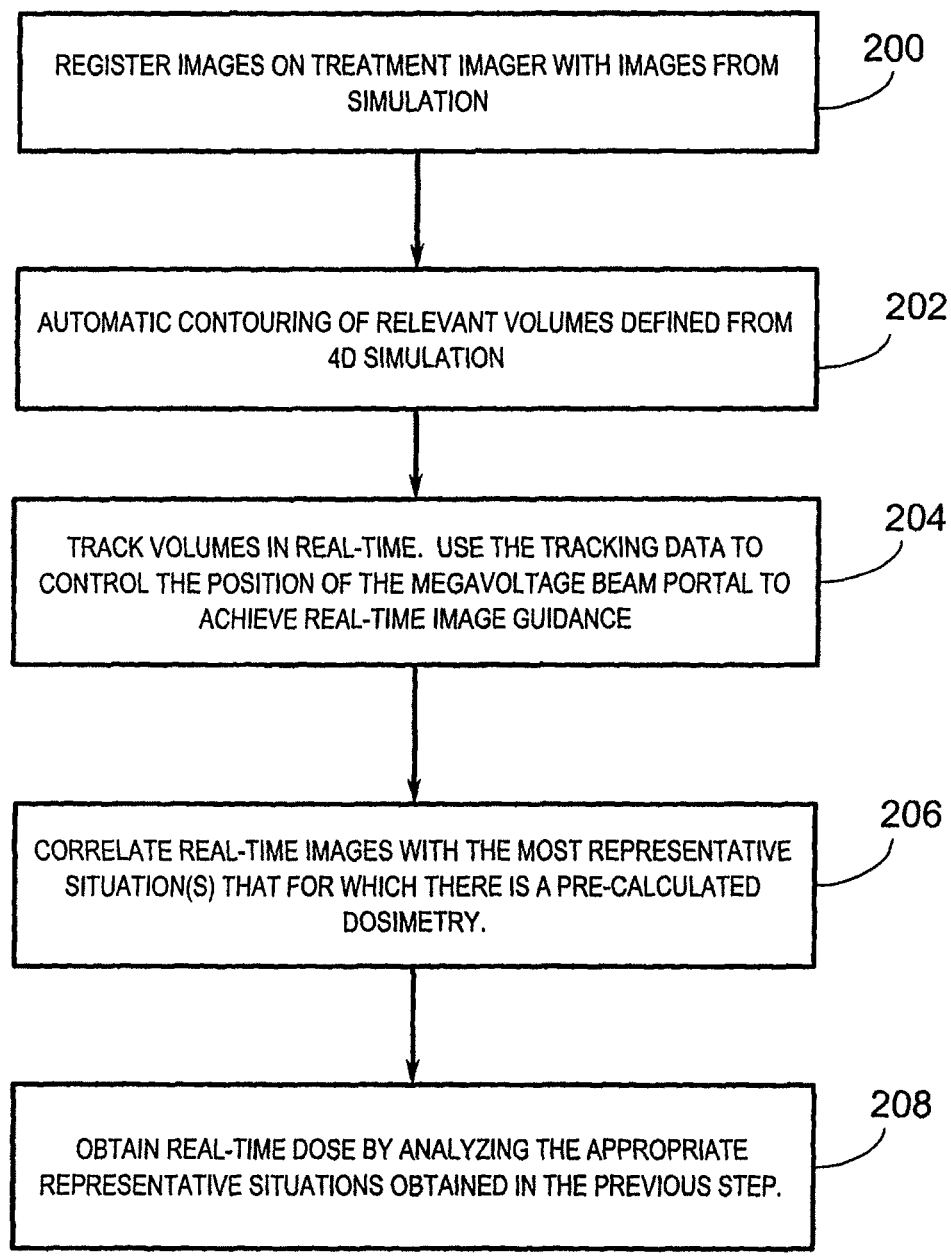
FIG. 5 is a flowchart showing the steps performed during radiation treatment to achieve real-time image guidance and three-dimensional dose reconstruction.

Turning now to FIGS. 2 to 4, an integrated linac and MRI system is shown and is generally identified by reference numeral 110. As can be seen, the integrated linac and MRI system 110 includes a linac 112 and an MRI apparatus 114.

In this particular example, the MRI apparatus 114 has a 0.2 T magnetic field strength and is of the open bore type including a table 116 on which a patient P can lay. The poles 118 and 120 of a polarizing magnet are disposed above and below the table 116. The linac 112 and magnet poles 118 and 120 are mounted on a rotating gantry 122 that is supported by a frame 124.

The linac 112 includes a head 128 housing an electron beam generator 130 mounted on an arm 132 that is affixed to the gantry 122. In this manner, the linac 112 rotates in unison with the gantry 122 and thus, maintains its position relative to the magnet poles 118 and 120. Of course if desired, the linac 112 may have its own gantry. In this case, the gantry of the linac 112 and the gantry 122 are mechanically coupled so that the linac 112 rotates in unison with the magnet poles 118 and 120.

The electron beam generator 130 includes an electron gun 133, an RF generator 134, an accelerating waveguide 136, a heavy metal target 138 at one end of the accelerating waveguide 136 and a beam collimating device (not shown). Interference reducing structure is also provided to inhibit the linac 112 and MRI apparatus 114 from interfering with one another during operation.

Alternatively, the linac 112 and MRI apparatus 114 may be mechanically coupled so that the electron beam is directed horizontally, and the magnet poles 118 and 120 are mounted vertically such that the magnetic field is horizontal, but perpendicular to the electron beam. These two components are fixed and non-movable. Variable angle electron or photon beam delivery is allowed by rotating the subject while in a sitting position. This integrated linac and MRI system configuration is particularly useful for lung cancer subjects who prefer standing/seating to laying supine, and for whom, conventional CT simulation does not allow simulation in the sitting position.

Further specifics of the integrated linac and MRI system 110 are described in Applicants' co-pending application filed on even date herewith and entitled "INTEGRATED EXTERNAL BEAM RADIOTHERAPY AND MRI SYSTEM", U.S. application Ser. No. 12/090,586, filed Oct. 23, 2008, now U.S. Patent Application Publication No. 2009/0149735, the content of which is incorporated by reference. Accordingly further specifics of the integrated linac and MRI systems will not be described further herein.

In order to provide four-dimensional image guidance at the time of treatment for real-time dose reconstruction, the MRI apparatus 114 is used to image the patient in 3D real-time at the time of treatment. The MRI apparatus 114 provides exquisite soft-tissue delineation with open bore. Using standard and deformable image registration methods, the MRI images are registered to the radiotherapy simulation images (see step 200 in FIG. 5) taken previously by the very high resolution MRI apparatus. Identification of the target tissue, the surrounding critical tissue and contours of the target and critical volumes are then automatically defined from the registered images (step 202). This tissue delineation permits the intra-fraction three-dimensional motion of all important tissues to be quantified and recorded in real-time. From the contours of the target and critical volumes, the target and critical volumes can be tracked in real-time (step 204). This target and critical volume tracking information is used to control operation of the linac 112 so that the photon beam emitted by the linac 112 is properly positioned thereby to achieve real-time image guidance.

Real-time images are then correlated with the most representative situations for which there is a pre-calculated dosimetry (step 206) and real-time radiation dose information is obtained by analyzing the appropriate most representative situations (step 208). Thus, radiation doses delivered to the patient can be reconstructed in three-dimensions and in real-time. This permits the treatment to be modified if the real-time radiation dose calculation predicts a dose that is outside of a tolerance and allows the radiation therapy to be adapted if the projected total cumulative radiation dose is out of tolerance.

As will be appreciated, the image guidance allows dose escalation to be performed in a safe way, since real-time dosimetry is available. In certain tissue sites, it has been shown that dose escalation will benefit survival. In the past, dose escalation could not be done safely, since tissue motion caused too large a PTV to be used, resulting in an unacceptable toxicity to the patient. The image guidance provides for the elimination of the PTV margin, thus yielding low radiation doses to surrounding tissues. Further, real-time dosimetry calculation allows alerts to be set when normal tissue reaches a tolerance dose, thereby protecting these tissues.

As will be appreciated, three-dimensional MRI imaging is used to simulate the radiotherapy treatment by processing, in three-dimensions and in real-time, the target and critical volumes and the maximum possible extensions of the target and critical volumes that are likely to occur during the treatment.

Although illustrative embodiments have been described herein with reference to the accompanying drawings and examples, it is to be understood that the disclosure is not limited to these embodiments, and various other changes and modifications may be affected therein by one skilled in the art without departing from the scope and spirit of the disclosure. All such changes and modifications are intended to be included within the scope of the disclosure as defined by the appended claims.

What is claimed is:

1. A radiation therapy treatment method comprising:
   imaging a subject to create subject images;
   processing the subject images to determine a four-dimensional simulation of movement of a target volume and a surrounding critical volume likely to occur during radiotherapy treatment, including a range of possible deviations of movement of the target volume and the critical volume from a mean trajectory;
   generating a treatment plan using at least the four-dimensional simulation; and
   during irradiation, further imaging the subject to create further subject images and also using the four-dimensional simulation and the treatment plan for tracking actual movement of the target volume and the critical volume and controlling the irradiation.

2. The radiation therapy treatment method of claim 1, further comprising:
reconstructing radiation doses delivered during irradiation in real-time based at least on the further imaging.

3. The radiation therapy treatment method of claim 2, further comprising:
modifying the irradiation in the event that delivered radiation doses are outside of tolerances.

4. The radiation therapy treatment method of claim 1, wherein the imaging and further imaging comprise capturing very high-resolution images of the target volume and the critical volume.

5. The radiation therapy treatment method of claim 1, wherein processing the subject images further comprises:
calculating a maximum possible target volume movement and a maximum possible critical volume movement; and
examining the maximum possible target volume movement and the maximum possible critical volume movement to determine if the target volume and the critical volume are likely to change over a selected period.

6. The radiation therapy treatment method of claim 5 further comprising:
repeating the imaging and the processing over a specified period when it is determined that the target volume and the critical volume are likely to change; and
determining an average four-dimensional simulation.

7. The radiation therapy treatment method of claim 6, wherein the specified period is several days when the selected period is day-to-day.

8. The radiation therapy treatment method of claim 5, wherein the treatment plan comprises photon fluence distributions and image guidance parameters and controlling the irradiation comprises selecting from photon fluence distributions and image guidance parameters based on an actual position of the target volume and the critical volume.

9. The radiation therapy treatment method of claim 5, further comprising generating data files comprising three-dimensional radiation dose distributions that cover a range of likely deviations.

10. The radiation therapy treatment method of claim 1, wherein the further imaging comprises:
registering the further subject images with the subject images that were processed to determine the four-dimensional simulation thereby to produce tracking information for the tracking.

11. The radiation therapy treatment method of claim 10, further comprising:
identifying target tissue of the target volume, surrounding critical tissue of the critical volume and contours of the target volume and the critical volume from the registered further subject images.

12. The radiation therapy treatment method of claim 11, further comprising reconstructing radiation doses delivered during irradiation in real time.

13. The radiation therapy treatment method of claim 12, further comprising modifying the irradiation being delivered if delivered radiation doses are outside of tolerances.

14. A radiation therapy treatment method, comprising:
imaging a subject to create subject images;
processing the subject images to determine a four-dimensional simulation of movement of a target volume and a surrounding critical volume likely to occur during radiotherapy treatment, including a range of possible deviations of movement of the target volume and the critical volume from a mean trajectory;
generating a treatment plan using at least the four-dimensional simulation;
generating a bank of radiation dose distributions covering the range of possible deviations; and
during irradiation:
further imaging the subject to create further subject images;
determining actual movement of the target volume and the critical volume based on the further subject images; and
retrieving a radiation dose distribution from the bank of radiation dose distributions when the actual movement of the target volume and the critical volume deviates from the treatment plan.

15. The radiation therapy treatment method of claim 14, further comprising storing the treatment plan and the bank of radiation dose distributions covering the range of possible deviations in one or more data files.

16. The radiation therapy treatment method of claim 14, further comprising:
modifying the irradiation in the event that radiation dose delivered is outside of tolerances.

17. The radiation therapy treatment method of claim 14, wherein the imaging and further imaging comprise capturing very high-resolution images of the target volume and the critical volume.

18. The radiation therapy treatment method of claim 14, wherein processing the subject images further comprises:
calculating a maximum possible target volume movement and a maximum possible critical volume movement; and
examining the maximum possible target volume movement and the maximum possible critical volume movement to determine if the target volume and the critical volume are likely to change over a selected period.

19. The radiation therapy treatment method of claim 18 further comprising:
repeating the imaging and the processing over a specified period when it is determined that the target volume and the critical volume are likely to change; and
determining an average four-dimensional simulation.

20. The radiation therapy treatment method of claim 19, wherein the specified period is several days when the selected period is day-to-day.

21. The radiation therapy treatment method of claim 14, wherein the treatment plan comprises photon fluence distributions and image guidance parameters to be used during irradiation.

22. The radiation therapy treatment method of claim 14, wherein the further imaging comprises:
capturing further subject images of the target volume and the critical volume; and
registering the further subject images with the subject images that were processed to determine the four-dimensional simulation thereby to produce tracking information for tracking the actual movement of the target volume and the critical volume.

23. The radiation therapy treatment method of claim 22, further comprising:
identifying target tissue of the target volume, surrounding critical tissue of the critical volume and contours of the target volume and the critical volume from the registered further subject images.

24. A radiation therapy treatment method comprising:
imaging a subject to create subject images;
processing the subject images to determine a four-dimensional simulation of movement of a target volume and a surrounding critical volume likely to occur during radiotherapy treatment by:

calculating a maximum possible target volume movement and a maximum possible critical volume movement;
generating a mean trajectory of the target volume and the critical volume together with a range of likely deviations of the target volume and the critical volume from the mean trajectory; and
examining the maximum possible target volume movement and the maximum possible critical volume movement to determine if the target volume and the critical volume are likely to change over a selected period;

generating a treatment plan using at least the four-dimensional simulation; and during irradiation, further imaging the subject to create further subject images and also using the four-dimensional simulation and the treatment plan for tracking actual movement of the target volume and the critical volume and controlling the irradiation.

\* \* \* \* \*